United States Patent [19]
Harris, Jr. et al.

[11] Patent Number: 5,779,709
[45] Date of Patent: Jul. 14, 1998

[54] ULNAR CUT GUIDE ALIGNMENT SYSTEM

[75] Inventors: Brian R. Harris, Jr., Memphis, Tenn.; Charles Sorbie, Kingston; Gerald A. B. Saunders, Sydenham, both of Canada

[73] Assignee: Wright Medical Technology, Inc., Arlington, Tenn.

[21] Appl. No.: 798,917

[22] Filed: Feb. 12, 1997

[51] Int. Cl.$^6$ .................................................. A61B 17/56
[52] U.S. Cl. .................................................. 606/87
[58] Field of Search ............................ 606/87, 88, 89, 606/86, 96, 97, 98, 79, 80

[56] References Cited

U.S. PATENT DOCUMENTS

| | | | |
|---|---|---|---|
| 4,242,758 | 1/1981 | Amis et al. | 606/87 |
| 4,624,250 | 11/1986 | Saunders et al. | 606/87 |
| 4,893,619 | 1/1990 | Dale et al. | 606/87 |
| 5,108,396 | 4/1992 | Lackey et al. | 606/62 |
| 5,628,749 | 5/1997 | Vendrely et al. | 606/80 |

*Primary Examiner*—Guy V. Tucker
*Attorney, Agent, or Firm*—Walker, McKenzie & Walker, P.C.

[57] ABSTRACT

An ulnar cut guide alignment system including an ulnar alignment guide having a first end for attachment relative to the proximal end of an ulna, a second end for attachment relative to the distal end of the ulna, and a long axis for placement parallel to the long axis of the ulna; an ulnar cut guide holder including a body having an aperture extending therethrough along a longitudinal axis; and an ulnar cut guide locator for connecting the ulnar cut guide holder to the ulnar alignment guide with the longitudinal axis through the aperture of the body of the ulnar cut guide holder placed substantially coextensive with the articular axis of the trochlear notch of the ulna when the first end of the ulnar alignment guide is attached relative to the distal end of the ulna and when the second end of the ulnar alignment guide is attached to the proximal end of the ulna.

3 Claims, 5 Drawing Sheets

U.S. Patent     Jul. 14, 1998     Sheet 1 of 5     5,779,709
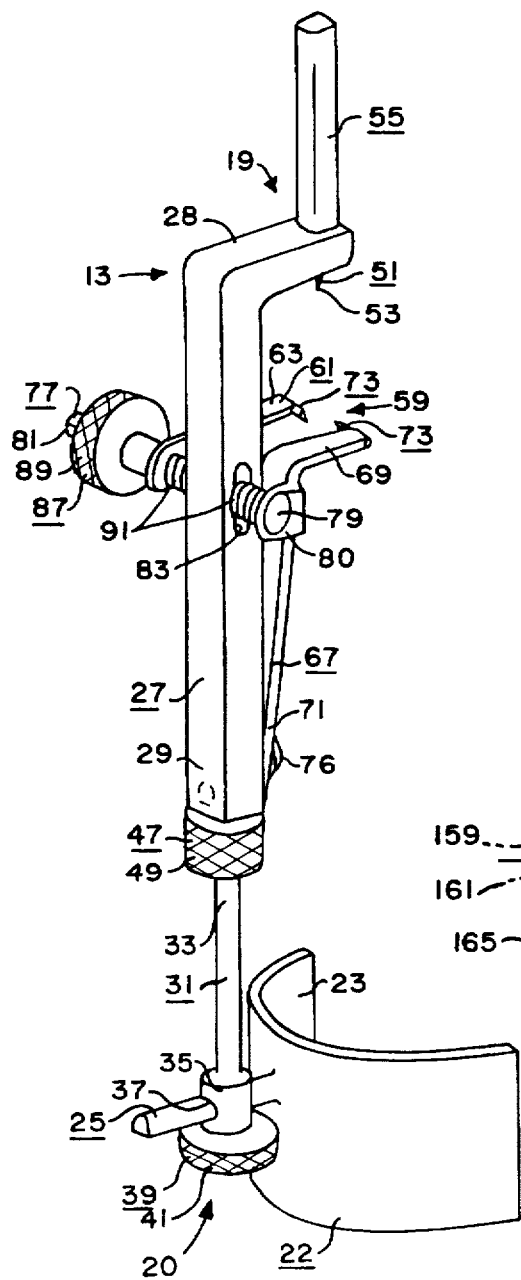
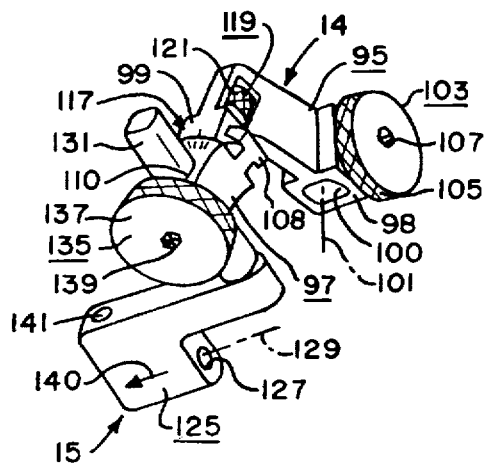
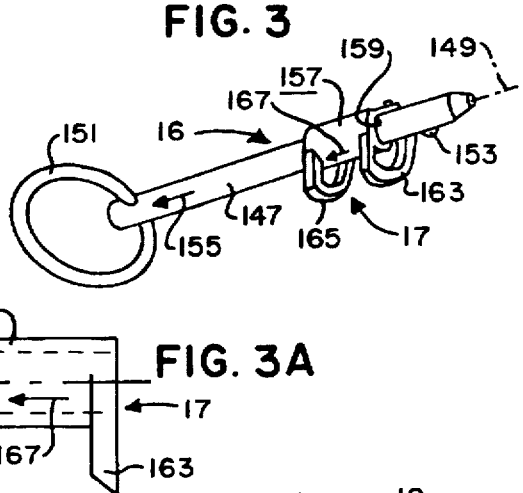
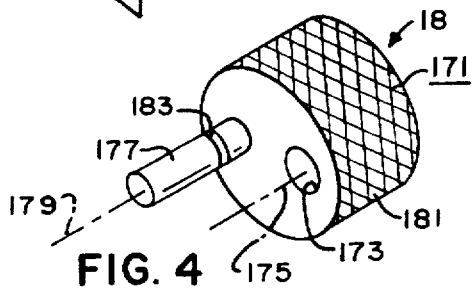

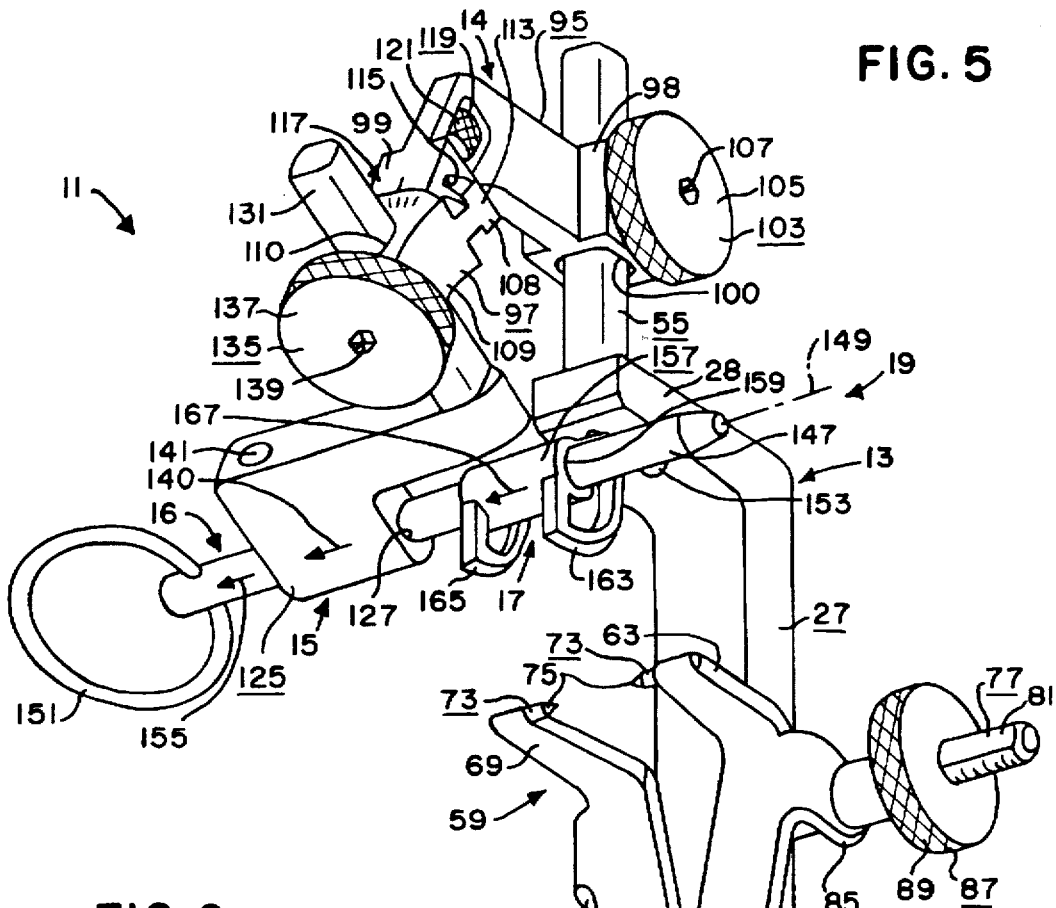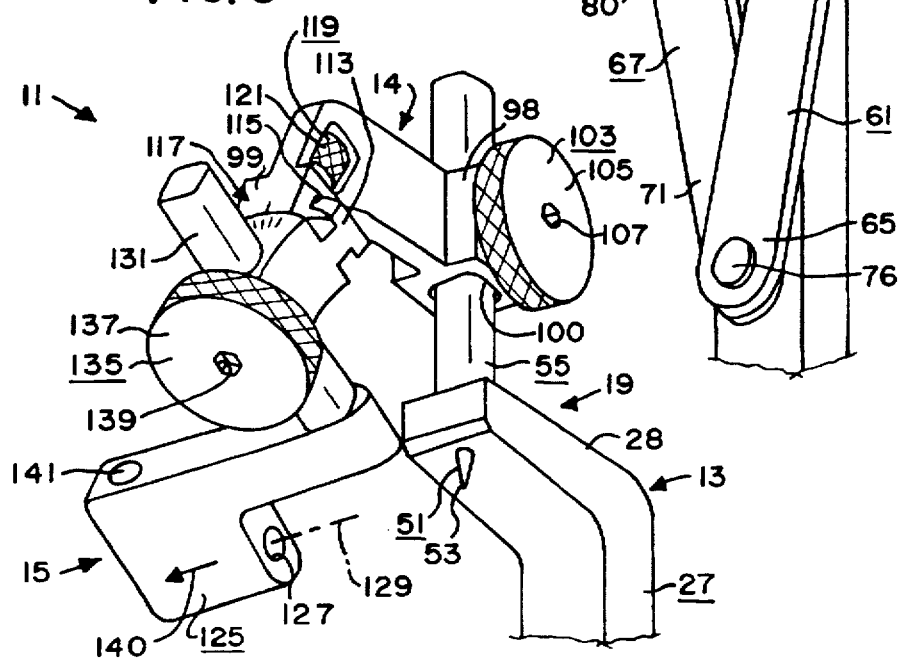

ULNAR CUT GUIDE ALIGNMENT SYSTEM

CROSS-REFERENCE TO RELATED APPLICATIONS Not Applicable.

STATEMENT RE FEDERALLY SPONSORED RESEARCH OR DEVELOPMENT Not Applicable.

REFERENCE TO A "MICROFICHE APPENDIX" Not Applicable.

BACKGROUND OF THE INVENTION

1. Field of the Invention:

The present invention relates, in general, to a system or apparatus for accurately guiding a cutting tool to prepare the proximal ulna for receiving an endoprosthesis.

2. Information Disclosure Statement:

The human elbow joint is formed by articulation of the distal humerus with both the proximal radius and the proximal ulna. Stability of the elbow joint depends on the shape of the joint articular surfaces and the functioning of ligaments and muscles surrounding the joint, etc. Repair of diseased or damaged elbow joints includes total elbow arthroplasty in which all of the articular surfaces of the elbow joint are resurfaced with implants.

Swanson, U.S. Pat. No. 4,280,231, issued Jul. 28, 1981, discloses an elbow prosthesis including a humeral component having a distal bearing surface for resurfacing the distal humerus, and an ulnar component having a proximal bearing surface for resurfacing the proximal ulna and for articulating with the distal bearing surface of the humeral component. The ulnar component also includes a distal bearing surface adapted to be abutted against by the proximal radius upon implantation.

Nothing in the known prior art discloses or suggests the present invention. More specifically, nothing in the known prior art discloses or suggests in ulnar cut guide alignment system including an ulnar alignment guide having a first end for attachment relative to the proximal end of an ulna, a second end for attachment relative to the distal end of the ulna, and a long axis for placement parallel to the long axis of the ulna; an ulnar cut guide holder including a body having an aperture extending therethrough along a longitudinal axis; and an ulnar cut guide locator for connecting the ulnar cut guide holder to the ulnar alignment guide with the longitudinal axis through the aperture of the body of the ulnar cut guide holder placed substantially coextensive with the articular axis of the trochlear notch of the ulna when the first end of the ulnar alignment guide is attached relative to the distal end of the ulna and when the second end of the ulnar alignment guide is attached to the proximal end of the ulna.

BRIEF SUMMARY OF THE INVENTION

One of the key aspects of a successful total elbow arthroplasty is the accurate anatomical positioning of the implant components. The location of the ulnar osteotomy is of fundamental importance to positioning the ulnar implant components. The present invention provides an apparatus for orienting a cutting guide used in the resection of the articular surface of an ulna. A basic concept of the present invention is to provide means of positioning an ulnar cutting guide relative to the ulna by referencing various anatomic landmarks including the distal forearm/wrist, the apex of the ulnar olecranon, the curvature of the olecranon and coronoid facets, and the orientation of the trochlear notch of the ulna.

The major object of the ulnar cut guide alignment system is to provide accurate anatomical positioning and location of a proximal ulnar osteotomy during total elbow arthroplasty by insuring accurate anatomical positioning of a cutting tool during proximal ulnar osteotomy.

The ulnar cut guide alignment system of the present invention includes, in general, an ulnar alignment guide, an ulnar cut guide locator, an ulnar cut guide holder, an ulnar rotation guide shaft, and an ulnar rotation guide.

The ulnar alignment guide is used to approximate the long axis of the ulna and provide a rigid platform onto which the ulnar cut guide locator is attached.

The ulnar cut guide locator approximates the angle of the trochlear notch relative to the long axis of the ulna, provides a means of adjusting the proximal-distal position of the articular surface osteotomy, and positions the ulnar cut guide holder.

The ulnar cut guide holder establishes the axis of rotation for the ulnar cutting guide relative to the trochlear notch and provides a means for adjusting the depth of cut of the articular surface osteotomy.

The ulnar rotation guide shaft slides through the ulnar cut guide holder to establish a temporary axial reference upon which the ulnar rotation guide is positioned.

The ulnar rotation guide is used to orient the axis of rotation of the ulnar cutting guide relative to the long axis of the ulna.

BRIEF DESCRIPTION OF THE SEVERAL VIEWS OF THE DRAWINGS

FIG. 1 is a perspective view of an ulnar alignment guide of the ulnar cut guide alignment system of the present invention.

FIG. 2 is a perspective view of an ulnar cut guide locator and an ulnar cut guide holder of the ulnar cut guide alignment system of the present invention, with the locator and holder combined with one another.

FIG. 3 is a perspective view of an ulnar rotation guide shaft and an ulnar rotation guide of the ulnar cut guide alignment system of the present invention, with the rotation guide shaft and rotation guide combined with one another.

FIG. 3A is an elevational view of the ulnar rotation guide of the ulnar cut guide alignment system of the present invention.

FIG. 4 is a perspective view of an ulnar cam for use with the ulnar cut guide alignment system of the present invention.

FIG. 5 is a perspective view of a portion of the ulnar alignment guide of the ulnar cut guide alignment system of the present invention, with the ulnar cut guide locator, ulnar cut guide holder, ulnar rotation guide shaft, and ulnar rotation guide of the ulnar cut guide alignment system of the present invention combined therewith.

FIG. 6 is a perspective view similar to FIG. 5 but with the ulnar rotation guide shaft and ulnar rotation guide removed from the other components.

DETAILED DESCRIPTION OF THE INVENTION

Figure 7:
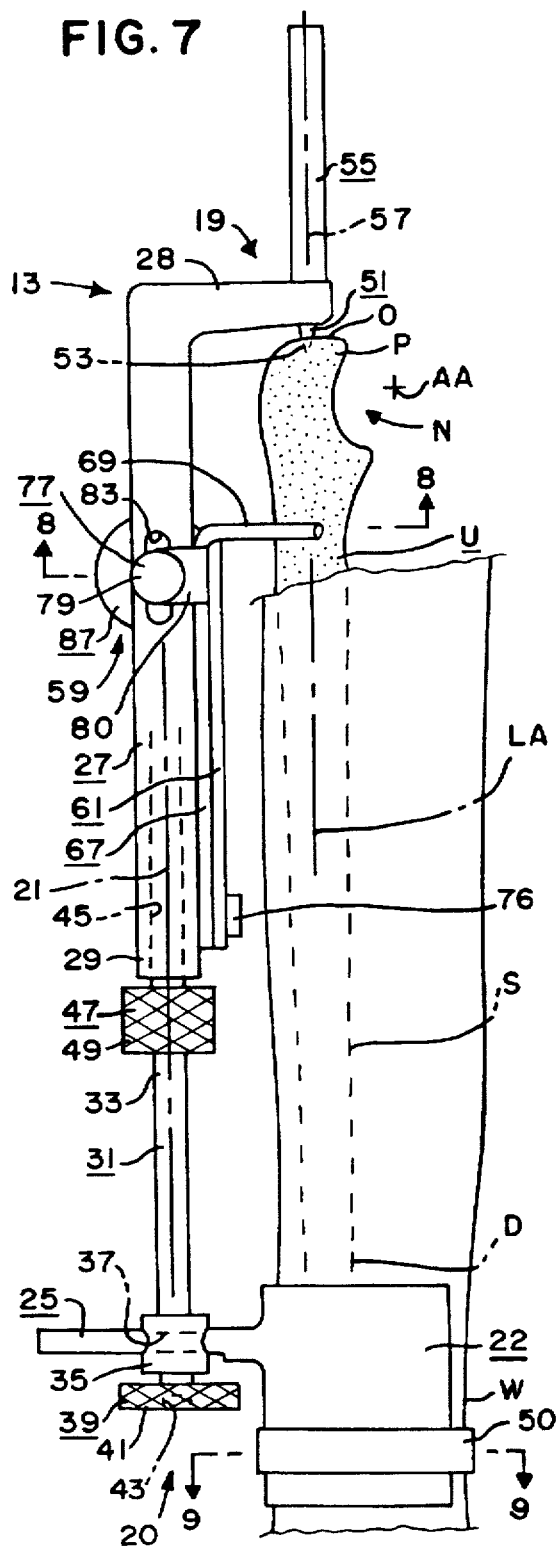
FIG. 7 is a somewhat diagrammatic side elevational view of the ulnar alignment guide of the ulnar cut guide alignment system of the present invention, shown secured to an ulna.
Figure 8:
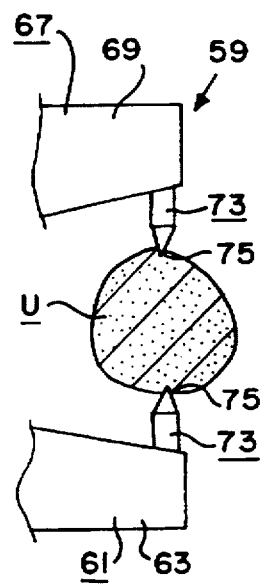
FIG. 8 is a sectional view substantially as taken on line 8—8 of FIG. 7, on an enlarged scale.

A preferred embodiment of the ulnar cut guide alignment system of the present invention is shown in the accompanying drawings, and identified by the numeral 11.

The ulnar cut guide alignment system 11 includes an ulnar alignment guide 13, an ulnar cut guide locator 14, an ulnar cut guide holder 15, an ulnar rotation guide shaft 16, and an ulnar rotation guide 17. The ulnar alignment guide 13 is used to approximate the long axis LA of an ulna U and provide a rigid platform onto which the ulnar cut guide locator 14 is attached. The ulnar cut guide locator 14 approximates the angle of the trochlear notch N of the ulna U relative to the long axis LA of the ulna U, provides a means of adjusting the proximal-distal position of the articular surface osteotomy, and positions the ulnar cut guide holder 15. The ulnar cut guide holder 15 establishes the axis of rotation for an ulnar cam or cutting guide 18 relative to the articular axis AA of the trochlear notch N and provides a means for adjusting the depth of cut of the articular surface osteotomy. The ulnar rotation guide shaft 16 slides through the ulnar cut guide holder 15 to establish a temporary axial reference upon which the ulnar rotation guide 17 is positioned. The ulnar rotation guide 17 is used to orient the axis of rotation of the ulnar cutting guide 18 relative to the long axis LA of the ulna U.

The ulnar cut alignment 13 has a first end 19 for attachment relative to the proximal end P of the ulna U, a second end 20 for attachment to the distal end D of the ulna U, and a long axis 21 between the first and second ends thereof for placement substantially parallel to the long axis LA of the ulna U.

The ulnar alignment guide 13 includes a cup member 22 that defines or forms the second end 20 of the ulnar cut alignment 13. The cup member 22 has a face surface 23 for attachment relative to the distal end D of the ulna U. More specifically, the face surface 23 of the cup member 22 encircles a portion of the distal end D of the ulna U, substantially adjacent the patient's wrist W. The ulnar alignment guide 13 further includes an elongated shaft 25 attached to the back side of the cup member 22, a generally L-shaped base or body 27 having a first end 28 and a second end 29 with a longitudinal axis extending from the second end 29 to the bend that forms the L-shape, and an elongated rod or slide 31 having a first end 33 adjustably attached to the second end 29 of the body 27 and a second end 35 adjustably attached to the shaft 25 with a longitudinal axis extending between the first and second ends 33, 35. The longitudinal axis of the body 27 extending from the second end 29 to the bend that forms the L-shape, and the longitudinal axis of the slide 31 extending between the first and second ends 33, 35, coact to form or define the long axis 21 of the ulna cut alignment 13.

The second end 35 of the slide 31 preferably has a transverse aperture 37 therethrough for slidably receiving the shaft 25 to allow the shaft 25, and thus the cup member 22, to be moved back and forth with respect to the longitudinal axis of the slide 31. The shaft 25 and/or aperture 37 may include means for preventing rotation of the shaft 25 within the aperture 37, etc. For example, the shaft 25 and the aperture 37 may have substantially matching transverse contours with non-circular cross sectional shapes and areas (e.g., each may have a flat along one of the sides thereof) as will now be apparent to those skilled in the art. A screw 39 is preferably provided for fixedly locking the shaft 25 to the slide 31. The screw 39 preferably includes structure (e.g., a knurled head 41) for allowing it to be easily hand tightened, and preferably includes structure (e.g., a hexagonal cavity 43) for allowing it to be firmly secured using a tool (e.g., a typical Allen or hex wrench).

The second end 29 of the body 27 preferably has an aperture 45 therein for slidably receiving the first end 33 of the slide 31 to allow the slide 31, and thus the cup member 22, to be moved back and forth with respect to the first end 28 of the body 27 so that the effective length of the ulnar alignment guide 13, i.e., the distance between the face surface 23 of the cup member 22 and the first end 28 of the body 27, can be varied. The second end 29 of the body 27 may have a collet-like portion (not shown), and a nut 47 may be provided for screwing on the collet-like portion to lock the slide 31 in place within the aperture 45 in the second end 29 of the body 27 as will now be apparent to those skilled in the art. The nut 47 preferably includes structure (e.g., a knurled surface 49) for allowing it to be easily hand tightened, etc.

The long axis 21 of the ulnar alignment guide 13 is thus defined or formed by the combination of the longitudinal axis of the body 27 and the longitudinal axis of the slide 31 when the slide 31 is positioned within the aperture 45, as will now be apparent to those skilled in the art.

An adjustable strap 50 or the like is preferably provided for extending around the cup member 22 and the patient's wrist W to help secure the cup member 22 (and thus the entire ulnar cut guide alignment system 11) to the patient's forearm. The strap 50 may consist of an elongated, flexible member having typical Velcro® type adjustable attachment structure on the opposite ends thereof to allow the effective length thereof to be easily varied as will now be apparent to those skilled in the art.

The ulnar alignment guide 13 includes a pin 51 attached to the first end 28 of the body 27. The pin 51 has a point 53 that is specifically designed for being driven into the olecranon process 0 of an ulna U for attachment to the proximal end P of the ulna U, and for thus defining or forming the first end 19 of the ulnar alignment guide 13.

The ulnar alignment guide 13 preferably includes a shaft 55 extending from the first end 28 of the body 27 opposite the pin 51 as clearly shown in the drawings. The shaft 55 has a longitudinal axis 57 that is aligned and coextensive with the longitudinal axis of the pin 51 and that is parallel to the longitudinal axis of the body 27. The shaft 55 preferably has a transverse contour with a non-circular cross sectional shape and area for reasons which will hereinafter become apparent. It should be noted that the shaft 55 and pin 51 are preferably constructed as a monolithic, one-piece, integral unit.

The ulnar alignment guide 13 preferably includes clamp means 59 for clamping onto the shaft S of the ulna U a distance below the proximal end of the ulna U. The clamp means 59 preferably includes a first arm member 61 having a first end 63 and a second end 65, and a second arm member 67 having a first end 69 and a second end 71. The first ends 63, 69 of the first and second arm members 61, 67 preferably terminate in a pin 73 having a point 75 for engaging the shaft S of the ulna U.

The clamp means 59 includes a pivot member 76 for pivotally attaching the second ends 65, 71 of the first and second arm members 61, 67 to the body 27 in such a manner that the points 75 of the pins 73 are directly opposite one another and can be moved toward and away from one another by moving the first ends 63, 69 of the first and second arm members 61, 67 toward and away from one another as will now be apparent to those skilled in the art. The pivot member 76 may consist of a bolt, pin or the like extending through the second ends 65, 69 of the arm members 61, 67 and into the body 27.

The clamp means 59 preferably includes control means for allowing the points 75 of the pins 73 to be moved toward and away from one another in a controlled manner. The control means may include a screw 77 having a head 79 attached to an ear or tab 80 of the second arm member 67 at a point spaced from the pivot member 76, and having a shaft 81 extending through a slot 83 in the body 27 between the first and second ends 28, 29 thereof, and through an ear or tab 85 of the first arm member 61 at a point spaced from the pivot member 76. The control means may include a nut 87 screwably attached to the distal end of the shaft 81 of the screw 77 for forcing the first ends 63, 69 of the first and second arm members 61, 67, and thus the points 75 of the pins 73, toward one another when the nut 87 is screwed further onto the shaft 81 as will now be apparent to those skilled in the art. The nut 87 preferably includes structure (e.g., a knurled portion 89) for allowing it to be easily hand tightened, etc. The control means may include coil springs 91 positioned about the shaft 81 between the body 27 and the tabs 80, 85 of the arm members 61, 67 to force or urge the first ends 63, 69 of the first and second arm members 61, 67, and thus the points 75 of the pins 73, apart from one another when the nut 87 is unscrewed on the shaft 81.

The ulnar cut guide locator 14 includes a first body member 95 for adjustable attachment to the ulnar alignment guide 13, and a second body member 97 for adjustable attachment to the first body member 95.

The first body member 95 preferably has a first end 98, a second end 99, and an aperture 100 through the first end 98 thereof. The aperture 100 is adapted to slide onto the shaft 55 of the ulnar alignment guide 13 so that the effective distance between the ulnar cut guide locator 14 and the point 53 of the pin 51 can be varied. The aperture 100 has a longitudinal axis 101 which will align with the longitudinal axis 57 of the shaft 55 when the first body member 95 is slide onto the shaft 55. The aperture 100 preferably has a transverse contour with a non-circular cross sectional shape and area which matches the cross section shape and area of the transverse contour of the shaft 55 to insure alignment of and prevent rotation between the first body member 95 and the shaft 55 as will now be apparent to those skilled in the art. A screw 103 is preferably provided for fixedly locking the first body member 95 to the shaft 55. The screw 103 preferably includes structure (e.g., a knurled head 105) for allowing it to be easily hand tightened, and preferably includes structure (e.g., a hexagonal cavity 107) for allowing it to be firmly secured using a tool (e.g., a typical Allen or hex wrench).

The second body member 97 preferably has a first end 108, a second end 109, and an aperture 110 through the second end 109 thereof. The aperture 110 has a longitudinal axis 111, and the first and second body members 95, 97 are preferably joined to one another in a manner to position the longitudinal axis 111 at an angle with respect to the longitudinal axis 101 of the aperture 100 through the first body member 95. The connection between the first and second body members 95, 97 preferably forms an angle adjuster for allowing pivotal movement therebetween so that the longitudinal axis 111 can be swung through an arc with respect to the longitudinal axis 101 and so that the carrying angle of the joint can determined and set based on the patient's anatomy as will hereinafter become apparent. More specifically, the first end 108 of the second body member 97 preferably has an arcuate flange 113, and the second end 99 of the first body member 95 preferably has an arcuate slot 115 and for slidably receiving the arcuate flange 113 so that the second body member 97 can be swung through an arc. Indicia markings 117 may be embossed or otherwise provided on adjacent portions of the second end 99 of the first body member 95 and the first end 108 of the second body member 97 for indicating the relative arcuate position of the first and second body members 95, 97 with respect to one another. Such indicia markings may be in 6° increments, etc. A positive locking mechanism (not shown) may be provided between the first and second body members 95, 97 for allowing substantially accurate angular adjustment between the first and second body members 95, 97 in, for example, 6 ° increments as will now be apparent to those skilled in the art. A screw 119 is preferably provided for fixedly locking the first and second body members 95, 97 together in the desired angular position. For example, the screw 119 may have a shaft (not shown) extending from the second end 99 of the body member 95 for being wedged against a portion of the arcuate flange 113 of the first end 108 of the second body member 97. The screw 119 preferably includes structure (e.g., a knurled head 121) for allowing it to be easily hand tightened.

The ulnar cut guide holder 15 includes a generally L-shaped body 125 having an aperture 127 extending therethrough along a longitudinal axis 129. An elongated shaft 131 extends from the body 125 along a longitudinal axis 133 that is transverse to the longitudinal axis 129 of the aperture 127. The shaft 131 is adapted to slide into the aperture 110 through the second body member 97 of the ulnar cut guide locator 14 so that the effective distance between the longitudinal axis 129 of the aperture 127 through the body 125 of the ulnar cut guide holder 15 and the long axis LA of the ulna U held by the ulnar alignment guide 13 can be varied. The shaft 131 preferably has a transverse contour with a non-circular cross sectional shape and area which matches the cross section shape and area of the transverse contour of the aperture 110 to insure alignment of and prevent rotation between the ulnar cut guide locator 14 and the shaft 131 as will now be apparent to those skilled in the art. A screw 135 is preferably provided for fixedly locking the ulnar cut guide locator 14 to the shaft 131. For example, the screw 135 may have a shaft (not shown) extending through the second end 109 of the body member 97 for being wedged against a portion of the shaft 131 of the ulnar cut guide holder 15. The screw 135 preferably includes structure (e.g., a knurled head 137) for allowing it to be easily hand tightened, and preferably includes structure (e.g., a hexagonal cavity 139) for allowing it to be firmly secured using a tool (e.g., a typical Allen or hex wrench). The body 125 may have an indicator mark 140 embossed or otherwise provided on the outer surface thereof for reasons which will hereinafter become apparent.

The ulnar cut guide holder 15 may include a ball plunger 141 mounted to the body 125 with the ball end 143 thereof extending into the aperture 127 for reasons which will hereinafter become apparent. Northwestern Tools Inc. manufactures such a ball plunger as vendor part number 33423P.

The ulnar rotation guide shaft 16 preferably includes an elongated shaft 147 extending along a longitudinal axis 149. The shaft 147 preferably has a transverse contour with a circular cross sectional shape that substantially matches the transverse contour of the aperture 127 in the body 125 of the ulnar cut guide holder 15. One end of the shaft 147 may be tapered to allow it to be easily inserted into the aperture 127. A pull ring 151 may be attached to the other end of the shaft 147 to allow it to be easily pulled from the aperture 127, etc. A ball-type plunger 153 may be provided in the shaft 147 adjacent the tapered end thereof for reasons which will hereinafter become apparent. The shaft 147 may have an indicator mark 155 embossed or otherwise provided on the outer surface thereof for reasons which will hereinafter become apparent. Such an ulnar rotation guide shaft 147 may consist of a ring-grip, quick release, self-locking pin as manufactured by McMaster-Carr, as product number 98404A150, or equivalent, with appropriate marking details added thereto.

The ulnar rotation guide 17 preferably includes a body 157 having an aperture 159 for slidably receiving the shaft 147. The aperture 159 preferably has a transverse contour with a circular cross sectional shape that substantially matches the transverse contour of the shaft 147 of the ulnar rotation guide shaft 16. The aperture 159 has a longitudinal axis 161. The ulnar rotation guide 17 preferably includes a first semicircular flange 163 extending from one end of the body 157, and a second semicircular flange 165 extending from the other end of the body 157. The first and second semicircular flanges 163, 165 are specifically designed, shaped and sized for being firmly pressed into the trochlear notch N of a typical ulna U. Thus, the first semicircular flange 163 may be slightly larger that the second semicircular flange 165 with the outer face of the first semicircular flange 163 forming a slightly shallower angle with respect to the longitudinal axis 161 of the aperture 159 than the outer face of the second semicircular flange 165 to accommodate that slightly different size and shape of the opposite sides of the typical trochlear notch N as will now be apparent to those skilled in the art. The body 157 may have an indicator mark 167 embossed or otherwise provided on the outer surface thereof for indicating the smaller second semicircular flange 165, and for other reasons which will hereinafter become apparent.

At least one ulnar cam or cutting guide 19 is provided for guiding a cutting tool T such as a high speed cutting burr relative to the trochlear notch N of the ulna U. The ulnar cam 18 includes a body 171 having an aperture 173 therethrough for receiving the cutting tool T, etc. The aperture 173 has a longitudinal axis 175. The ulnar cam 18 includes an elongated shaft 177 extending along a longitudinal axis 179. One end of the elongated shaft 177 is attached to the body 171 with the longitudinal axis 179 parallel with and spaced from the longitudinal axis 175 of the aperture 173. The shaft 177 preferably has a transverse contour with a circular cross sectional shape that substantially matches the transverse contour of the aperture 127 through the body 125 of the ulnar cut guide holder 15. The body 171 is preferably designed to allow it to be easily rotated about the longitudinal axis 179 of the shaft 177. For example, the body 171 may be disk-shaped and the sides thereof may include structure (e.g., a knurled surface 181) for allowing it to be easily rotated by hand, etc. The shaft 177 preferably has a detent or groove 183 extending therearound as clearly shown in FIG. 4 for reasons as will hereinafter become apparent. Different size ulnar cams (e.g. small, medium and large) with different distances between the longitudinal axis 175 of the aperture 173 and the longitudinal axis 179 of the shaft 177, are preferably provided to accommodate different patient size, etc.

The use of the ulnar cut guide alignment system 11 of the present invention is typically part of a total elbow arthroplasty. Such total elbow arthroplasty may start with standard preoperative planning to estimate the size of the prostheses to be implanted, etc. Using a posterio-lateral approach, an incision is made on the posterio-lateral aspect of the elbow. The incision begins opposite the junction of the middle and distal thirds of the humerus in the midline of the posterior surface of the arm. The incision curves laterally one centimeter posterior to the lateral epicondyle and then medially to end over the subcutaneous border of the ulna U. The distal end of the incision is at the junction of the upper and middle thirds of the ulna U.

The interval between the brachio-radialis and the lateral edge of the triceps is defined and the muscles separated. The separation is continued down the lateral border of the humerus to the origin of the anconeus and the interval between anconeus and the extensor carpi ulnaris.

The extensor muscles are eased off the anterolateral aspect of the humerus. The common extensor origin is lifted off the lateral epicondyle and the lateral collateral ligament by sharp dissection. The capsule of the elbow and the annular ligament are excised to expose the neck of the radius.

The anconeus muscle is sharply dissected from its origins behind and below the lateral epicondyle and separated from the extensor carpi ulnaris distally to the ulna U. The nerve to the anconeus is a continuation of the branch of the radial nerve which begins at the upper end of the spiral groove and passes through the medial head of triceps, which it supplies. Damage to the nerve can be avoided by taking the anconeus postero-medially. The elbow can then be dislocated to expose the radial head, the olecranon process O and trochlear notch N or sigmoid fossa of the ulna U and the distal end of the humerus.

The humerus can be then prepared depending on the type prosthesis to be implanted, etc.

Figure 9:
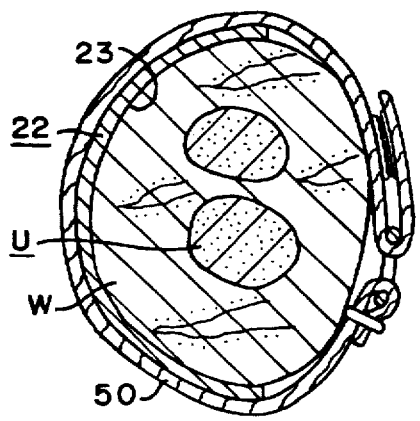
FIG. 9 is a sectional view substantially as taken on line 9—9 of FIG. 7, on an enlarged scale.
Figure 10:
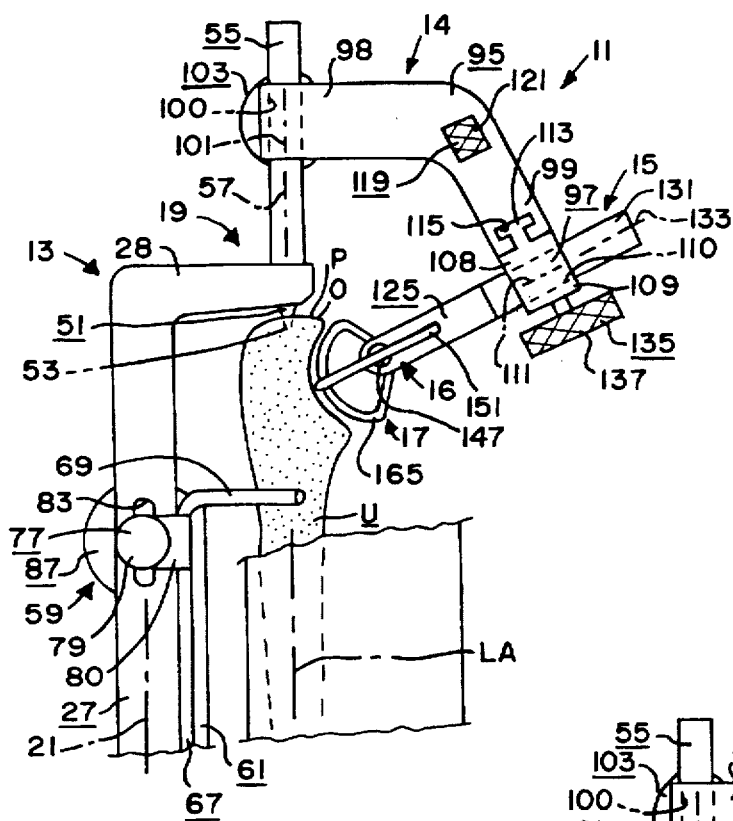
FIG. 10 is a somewhat diagrammatic side elevational view of a portion of the ulnar alignment guide of the ulnar cut guide alignment system of the present invention, similar to FIG. 7 but showing the ulnar cut guide locator, ulnar cut guide holder, ulnar rotation guide shaft, and ulnar rotation guide of the ulnar cut guide alignment system of the present invention combined therewith.
Figure 11:
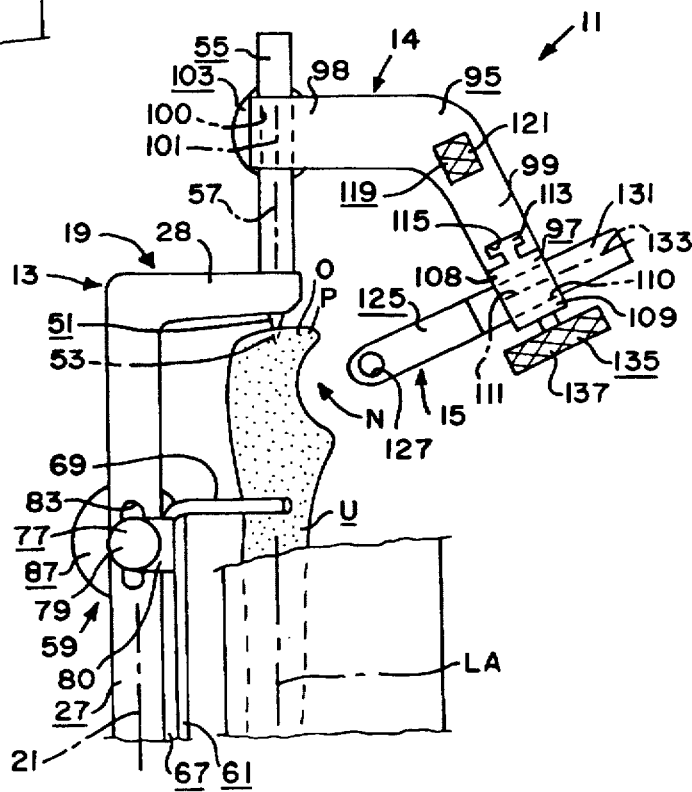
FIG. 11 is similar to FIG. 10 but with the ulnar rotation guide shaft, and ulnar rotation guide of the ulnar cut guide alignment system of the present invention removed from the other components.
Figure 12:
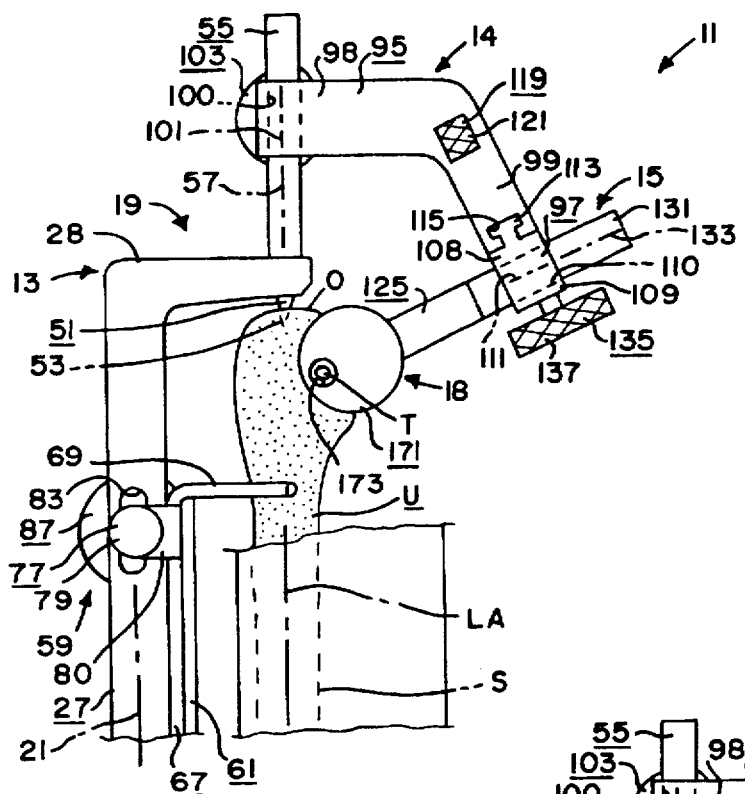
FIG. 12 is similar to FIG. 11 but with the ulnar cam mounted on the ulnar cut guide holder of the ulnar cut guide alignment system of the present invention, and with a cutting tool combined therewith.
Figure 13:
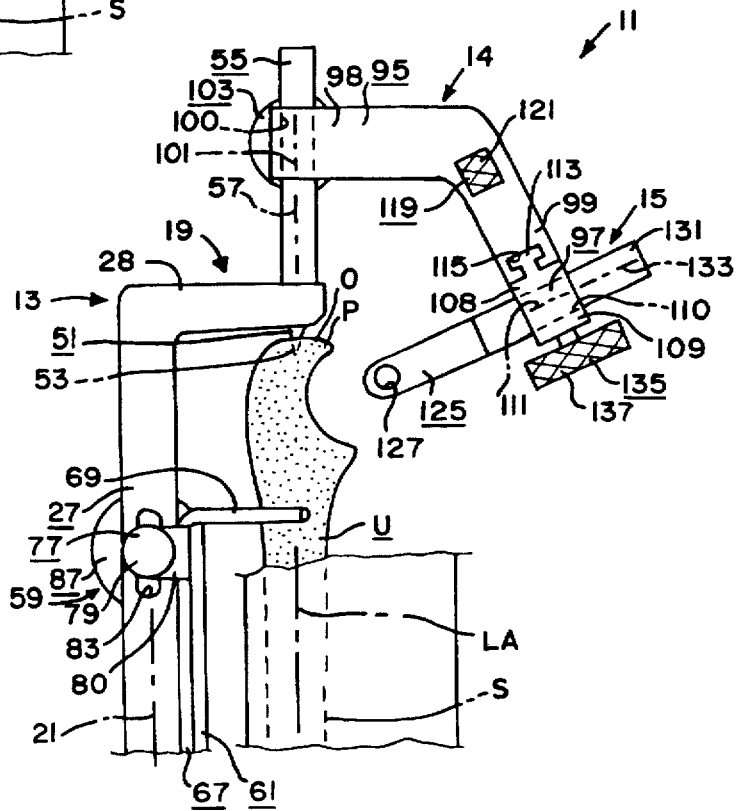
FIG. 13 is similar to FIG. 10 but shows after an articular surface osteotomy of the proximal ulna.

To then prepare the ulna U, the ulnar alignment guide 13 is first positioned with the point 53 of the pin 51 thereof engaging the olecranon process O of the ulna U, and with the long axis 21 of the ulnar alignment guide 13 (i.e., the longitudinal axes of the body 27 and the longitudinal axis of the slide 31) substantially parallel to the long axis LA or shaft S of the ulna U. The point 53 of the pin 51 can then be impacted in the center of the olecranon process O using a plastic ended mallet or the like on a the first end 28 of the body 27 of the ulnar cut guide holder 15, etc. The effective length of the ulnar alignment guide 13 can be adjusted to a suitable length for the patient's forearm to locate the face surface 23 of the cup member 22 adjacent the patient's wrist W by, if necessary, moving the shaft 25 in the aperture 37 and by moving the slide 31 in the aperture 45. Once the cup member 22 is properly positioned, the screw 39 and nut 47 can be tightened to lock the shaft 25 and slide 31 in position. The strap 50 can then be applied around the cup member 22 and the patient's wrist W as shown in FIG. 7 and 9 to secure the patient's wrist W to the cup member 22. The whole ulnar alignment guide 13 can be rotated in a medial or lateral direction to be aligned parallel with the subcutaneous border of the ulna U. The nut 87 of the clamp means 59 is then lightly tightened to cause the points 75 of the pins 73 of the arm members 61, 67 to engage the shaft S of the ulna U. With the ulnar alignment guide 13 thus positioned on the ulna U, the longitudinal axis 57 of the shaft 55 will be substantially aligned and coextensive with the long axis LA or shaft S of the ulna U.

The ulna cut guide locator 14 and ulna cut guide holder 15 are pre-assembled by extending the shaft 131 of the ulnar cut guide holder 15 into the aperture 110 through the second end 109 of the second body member 97 of the ulnar cut guide locator 14, and then lightly tightening the screw 135, thereby forming a construct as shown in FIG. 2. The elongated shaft 147 of the ulnar rotation guide shaft 16 can then be inserted through the aperture 127 in the body 125 of the ulnar cut guide holder 15, and then through the aperture 159 in the body 157 of the ulnar rotation guide 17. The ball-type plunger 153 of the ulnar rotation guide shaft 16 will then serve to hold the shaft 147, the ulnar cut guide holder 15, and the ulnar rotation guide 17 together. The angle adjuster between the first and second body members 95, 97 can be moved to the 6° position until all other parts of the assembly are tightened. Once the assembly is in place, the screw 119 between the first and second body members 95, 97 can be loosened, allowing the carrying angle of the joint to be determined by the patients anatomy. The screw 119 can then be tightened.

The thus-assembled construct (i.e., the ulnar cut guide locator 14, the ulnar cut guide holder 15, the ulnar rotation guide shaft 16, and the ulnar rotation guide 17) can then be attached to and combined with the ulnar alignment guide 13 by merely inserting shaft 55 of ulnar alignment guide 13 through the aperture 100 of the first body member 95 of the ulnar cut guide locator 14. The indicator marks (arrows) 140, 155, 167 of the ulnar cut guide holder 15, the ulnar rotation guide shaft 16, and the ulnar rotation guide 17, respectively, can be used for indicating the proper positioning direction of the various components. More specifically, the various components should be assembled with all the indicator marks 140, 155, 167 pointing in the same direction (see FIG. 5), i.e., toward the radial (lateral) side of the ulna U.

The ulnar cut guide locator 14 can then be moved back and forth on the shaft 55 of the ulnar alignment guide 13, the second body member 97 of the ulnar cut guide locator 14 can be pivoted relative to the first body member 95 thereof, and the ulnar cut guide holder 15 can be moved back and forth in the aperture 110 through the second end 109 of the second body member 97 until the flanges 163, 165 of the ulnar rotation guide 17 are eased into position, firmly pressed into the trochlear notch N of the ulna U. Minor adjustments may then be made to suit individual clinical situations. Once the surgeon is satisfied with the positions, all the various knurled knobs (i.e., the screw 39, the nut 47, the nut 87, the screw 103, the screw 119, and the screw 135) are firmly tightened, using a tool (e.g., a typical Allen or hex wrench) where appropriate.

The ulnar rotation guide shaft 16 and the ulnar rotation guide 17 are then removed from the ulnar cut guide holder 15 by merely pulling the shaft 147 out of the aperture 127. An ulnar cam 18 of appropriate size is then mounted on the ulnar cut guide holder 15 by merely inserting the shaft 177 of the ulnar cam 18 into the aperture 127 of the body 125 of the ulnar cut guide holder 15. The ball plunger 141 of the ulnar cut guide holder 15 will engage the groove 183 in the shaft 177 of the ulnar cam 18 to hold the ulnar cam 18 to the ulnar cut guide holder 15 while allowing the ulnar cam 18 to be rotated about the longitudinal axis 179 of the shaft 177.

The cutting tool T, etc., can then be passed through the aperture 173 in the body 171 of the ulnar cam 18, and an arc described against the lateral side of the trochlear notch N of the ulna U. Small adjustments can be made to ensure a coincident cutting arc and the amount of bone to be removed.

The damaged joint surface of the ulna U can then be removed by rotating the body 171 of the ulnar cam 18, causing the cutting tool T to move in an arc about the longitudinal axis 179 of the shaft 177. When cutting is complete, the ulnar cut guide alignment system 11 should be removed from the ulna U as a unit, thereby allowing all previously set angles to remain intact should minor adjustments need to be made at a later time.

Final preparation of the ulna U may include opening and reaming the intramedullary canal of the ulna U, etc. Trial components may then be placed firmly in position and the elbow joint reduced. A full range of flexion and extension, supination and pronation should be attempted to ensure general stability and proper orientation of the components. After any necessary or desired adjustments, the trial components are removed, the cut bone surfaces and humeral medullary canal are thoroughly lavaged, and permanent prostheses are then implanted in any typical manner. After final testing for motion and stability, the surgical site can be cared for and closed in any typical manner.

Although the present invention has been described and illustrated with respect to a preferred embodiment and a preferred use therefor, it is not to be so limited since modifications and changes can be made therein which are within the full intended scope of the invention.

We claim:

1. An ulnar cut guide alignment system for use in the osteotomy of an ulna having a proximal end, a distal end, a long axis extending between the proximal and distal ends, and an trochlear notch having an articular axis; the ulnar cut guide alignment system comprising:

(a) an ulnar alignment guide having a first end for attachment relative to the proximal end of the ulna, a second end for attachment relative to the distal end of the ulna, and a long axis for placement parallel to the long axis of the ulna;

(b) an ulnar cut guide holder including a body having an aperture extending therethrough along a longitudinal axis;

(c) ulnar cut guide locator for connecting the ulnar cut guide holder to the ulnar alignment guide with the longitudinal axis through the aperture of the body of the ulnar cut guide holder placed substantially coextensive with the articular axis of the trochlear notch of the ulna when the first end of the ulnar alignment guide is attached relative to the distal end of the ulna and when the second end of the ulnar alignment guide is attached to the proximal end of the ulna;

(d) ulnar rotation guide for positioning in the trochlear notch of the ulna; and (e) an ulnar rotation guide shaft for attaching the ulnar rotation guide to the ulnar cut guide holder along the longitudinal axis of the aperture in the ulnar cut guide holder.

2. The ulnar cut guide alignment system of claim 1 in which the ulnar rotation guide includes a body, a first semicircular flange extending from one end of the body, and a second semicircular flange extending from the other end of the body.

3. The ulnar cut guide alignment system of claim 2 in which the first semicircular flange of the ulnar rotation guide is larger that the second semicircular flange of the ulnar rotation guide.

* * * * *